United States Patent [19]

Zachariades et al.

[11] Patent Number: 5,479,952
[45] Date of Patent: Jan. 2, 1996

[54] DENTAL FLOSS OF ULTRA-HIGH MODULUS LINE MATERIAL WITH ENHANCED MECHANICAL PROPERTIES

[75] Inventors: Anagnostis E. Zachariades, Hillsborough; Premal Shukla, Foster City, both of Calif.

[73] Assignee: Polteco, Inc., Hayward, Calif.

[21] Appl. No.: 393,548

[22] Filed: Feb. 23, 1995

Related U.S. Application Data

[62] Division of Ser. No. 177,905, Jan. 6, 1994, Pat. No. 5,407,623.

[51] Int. Cl.⁶ ..................................................... A61C 15/00
[52] U.S. Cl. ............................................................. 132/321
[58] Field of Search ..................................... 132/321, 323

[56] References Cited

U.S. PATENT DOCUMENTS

| | | | |
|---|---|---|---|
| 3,800,812 | 4/1974 | Jaffe | 132/321 |
| 3,943,949 | 3/1976 | Ashton et al. | 132/321 |
| 4,033,365 | 7/1977 | Klepak et al. | 132/321 |
| 5,033,488 | 7/1991 | Curtis et al. | 132/321 |
| 5,113,880 | 5/1992 | Honda et al. | 132/321 |
| 5,220,932 | 6/1993 | Blass | 132/321 |
| 5,279,314 | 1/1994 | Poulos et al. | 132/325 |

*Primary Examiner*—Cary E. O'Connor
*Attorney, Agent, or Firm*—Owen, Wickersham & Erickson

[57] ABSTRACT

A method of producing high modulus and high strength products of polyethylene and other thermoplastic polymers by swelling with a suitable solvent a melt crystallized, or compacted powder morphology to form a pseudo-gel, drying the pseudo-gel, compressing it, and drawing it. The optimum process involves swelling the initial morphology in the form of a tape/ribbon/rod/monofilament/sheet/tube in a non-volatile solvent at temperatures near the polymer crystalline melting point, cooling the morphology under controlled conditions, lightly compressing it to remove the non-volatile solvent, extracting the non-volatile solvent by volatile solvent, removing the volatile solvent by evaporation or vacuum, compressing the morphology between rolls, and then stretching it at temperatures below the crystalline melting point of the polymer to obtain tapes, ribbons, monofilaments, sheets or tubes with improved mechanical properties. Products from the method include improved dental floss, fishing line and numerous other applications.

5 Claims, No Drawings

DENTAL FLOSS OF ULTRA-HIGH MODULUS LINE MATERIAL WITH ENHANCED MECHANICAL PROPERTIES

This is a divisional of application Ser. No. 08/177,905 filed on Jan. 6, 1994, now U.S. Pat. No. 5,407,623.

FIELD OF THE INVENTION

This invention relates to improved high molecular weight polyethylene tape, ribbon or line products with continuous and coherent structures having high modulus and tensile strength properties and particularly adaptable for use as dental floss, fishing line and other line products. The invention also relates to a novel method for processing ultra-high molecular weight polyethylene (UHMWPE) morphologies and other polymers for producing such products having high modulus and tensile strength properties.

BACKGROUND OF THE INVENTION

Ultra-high molecular weight polyethylene (UHMWPE) is a unique polymer with outstanding properties. It can be compression molded to obtain products which have high abrasion, wear, and fatigue resistance and strength. Also, it can be processed by solution techniques and drawn to form ultra-high modulus and strength multifilament fibers. Specially prepared single crystal morphologies of this polymer can be extruded and drawn to produce fibers with a modulus approaching theoretically predicted values. UHMWPE is intractable by conventional melt processing techniques such as extrusion and injection molding because of its extremely high molecular weight and melt viscosity, and is processed by powder sintering techniques used for ceramics and metals, and by ram extrusion.

Information in the prior art is available separately on the swelling behavior of crosslinked systems in the presence of a solvent, the dissolution of polymers, and the diffusion of solvents into amorphous polymers. However, there is only limited information in the literature on simultaneous kinetics of swelling and dissolution in polymers. Ultra-high molecular weight polymers are unique in the respect that significant swelling can occur without dissolution, even though the polymers are uncrosslinked and are crystalline in nature. This phenomenon occurs because of the long reptation and relaxation times of the molecular chains and the high molecular chain entanglement concentrations in these systems.

There has been extensive investigation on producing high modulus and high strength products from flexible and linear commodity polymers. In Zachariades patents Nos. 5,030,402 and 4,820,466 solid-state deformation processes are disclosed for achieving high modulus products. Smith et al (P. Smith and P. Lemstra, J. Mater. Sci., 1980, Vol. 15, 505 and P. Smith and P. Lemstra British Polymer Journal, 1980, 212) among others reported the gel processing route for the manufacture of high stiffness and strength ultra-high molecular weight polyethylene fibers. This process required the polymer to be dissolved in a solvent, extruded, quenched, freed of the solvent and then subsequently hot drawn. In U.S. Pat. No. 4,413,110, Kavesh et al also described gel spinning from a solution to make ultra-high modulus and strength polyethylenes using 2–5% UHMWPE in paraffin oil. Such a process uses too much solvent making processing difficult. Tapes made from melt crystallizing UHMWPE exhibit draw ratios of only about 8, resulting in final properties of Young's modulus about 1–2 GPa and tensile strength of 0.1–0.3 GPa.

Zachariades in his earlier patent, 4,655,769, differentiated between pseudo-gels and true gels used by other researchers, and described a process for making ultra-high polyethylene tubular products employing pseudo-gel states covering the following salient step points:

Dissolving a starting material of UHMWPE powder in non-volatile solvent at 140°–170° C. to produce a solution; cooling the solution to 123° C. to prepare a pseudo-gel in sheet form; extracting non-volatile solvent by a volatile solvent; compressing the pseudo-gel at 123° C. to form a thin gel-like film which is wrapped around a mandrel; evaporating the volatile solvent while the pseudo-gel film is wrapped on the mandrel; and then drawing the tubular product at around 5× at 135° C.

Also, others have attempted to develop polymer products with high strength characteristics. In Sano et al U.S. Pat. Nos. 4,879,076, 5,026,511, 4,996,011, 4,760,120 and 5,002,714, a selected polyethylene obtained using a specific catalyst was drawn at temperatures lower than the polymer melting point, in order to make high modulus and high strength fibers or films. In some cases this specific polyethylene was compression molded, immersed in solvent, solid-phase extruded or rolled, and finally drawn. Their process is similar to an earlier process, (See 1. M. P. C. Watts, A. E. Zachariades and R. S. Porter, "New Methods of Production of Highly Oriented Polymers" in "Contemporary Topics in Polymer Science" Ed: M. Shen, Plenum Press, 1979, p. 297–318 and A. E. Zachariades U.S. Pat. No. 4,820,466). Kobayashi et al in their U.S. Pat. Nos. 5,106,555 and 5,200,129 describe a process for continuous production of polyolefin material by feeding the powder between a pair of belts under compression rolling and stretching the compression-molded olefin.

Mackley and Solbai in their published paper (Mackley, Malcolm R., and Solbai, Somad, "Swell Drawing: A new method of manufacturing high performance polyethylene structures", in Polymer J., 1987, Vol. 28, 1115–1120) present a process of swell drawing to manufacture high modulus and high strength ultra-high molecular weight polyethylene (UHMWPE) tapes. Their process includes the following steps:

1. Preparing a precursor UHMWPE material stock (Hoechst Celanese GUR 415) without orientation using sintering by ram extrusion. Preparation of tapes of thickness 0.010 inch by skiving the UHMWPE stock.
2. Swelling the skived tape in decalin or xylene at 100°–130° C. for 1 to 10 minutes to an extent that the weight of the solvent to weight of the polymer Ws/Wp, was up to 20.
3. Cooling the swollen tape down to room temperature under uncontrolled conditions to crystallize the swollen UHMWPE.
4. Evaporating the volatile solvent from the polymer at 80° C.
5. Drawing the dried tape under isothermal conditions at 4 inch/min (100 mm/min) in the temperature range of 90°–120° C.

SUMMARY OF THE INVENTION

The present invention is different from the aforesaid prior art including Mackley and Solbai's process and produces a different and improved result because it uses different precursor morphologies to form a pseudo-gel, different swelling conditions, different polymers, and different processing steps.

The present process includes the formation of a pseudo gel state in the form of a swollen tape (or ribbon), using a non-volatile solvent, the compression of the swollen tape, the extraction of non-volatile solvent with a volatile solvent from the pseudo-gel state, the evaporation of the volatile solvent from the pseudo-gel state to form a dried tape, compression deformation of the dried tape between rollers, and then high temperature drawing or stretching to obtain high modulus and high strength products. The present process does not deal with dissolution of the polymer or fluid processing, as has been described by earlier authors and patents, but deals with the controlled swelling of a thermoplastic polymer as it forms a pseudo-gel with a crystalline structure while the solvent is incorporated in the polymer, then removing the solvent to produce a more crystalline morphology, then compressing this crystalline morphology between compression rolls, and finally solid state deforming (e.g. by stretching) the crystalline morphology from the pseudo-gel precursor to obtain products with high modulus and strength properties. The starting material in the present process can be in the form of skived tape from a melt crystallized material stock, melt crystallized tape as produced by melt extrusion, compacted powder morphology or sintered powder morphology. Depending on their width, we observe that tapes obtained by skiving of melt crystallized stock often exhibit surface defects along the length of the tape which can be detrimental in the subsequent drawing (stretching) step of the process.

The amount of swelling during the formation of the pseudo-gels can also be controlled by the degree of crystallinity of the starting polymer profile. A lower crystallinity, associating with a higher amorphous region, allows more swelling. A major advantage of the present process is that use of solvents for the formation of the pseudo-gel state by swelling a polymer is limited to small amounts and does not require so-called "solution processing" of the polymer. Upon swelling of a polymer in a solvent around the crystalline melting temperature of the polymer, the density of the molecular chain entanglements is reduced, thus making it easier to extend the molecular chains on stretching the polymer to a high draw ratio after the removal of the solvent from it and producing e.g. tapes and ribbons with high modulus and strength. To attain high modulus and strength performance with a draw ratio, upon stretching in the solid state, it is important that the molecular chains between adjoining crystal be intertwined together just enough to enable efficient drawing and extension of the molecular chains to take place without the chains slipping on one hand or without the molecular entanglements preventing their draw. In an analogy to cooked spaghetti which is mixed up with sauce, under the condition of the limited amounts of solvent and short times allowed for solvent treatment in our process, the molecular chains become "lubricated" and disentangle to an extent which is controlled by the degree of crystallinity of the pseudo-gel state. The "solvent-lubrication" process is reversible in that it does not occur when the solvent is removed from the polymer.

In summary, the present invention provides high modulus and high strength tape, ribbon or line products from thermoplastic linear polymers capable of being swollen in a suitable solvent to form a pseudo-gel state and, upon removal of the solvent by extraction or evaporation, of being solid state deformed by compression (e.g. extrusion or rolling), and then by tension (stretching). Not all thermoplastic polymers are capable of being swollen with a solvent and forming a pseudo-gel state, namely a state with time dependent elastic properties, and in addition of being solid state deformed into high modulus and strength fibrous products. Polymers which meet these requirements must be linear and have a very high molecular weight or polar groups in the chain backbone such as the polyamides. By polymers having a very high molecular weight, it is meant, a polymer resin having a molecular weight (as measured by viscometric techniques) of at least 300,000 and up to 5–6 million. Polymers which can be used under the scope of this invention include polymers such as polyethylenes including the UHMWPE meeting the specification of ASTM D4020-81, polypropylene, poly(L-lactide), poly(vinyl alcohol), polyacrylonitrile, poly-4-methyl-1-pentene, poly(ethylene terphthalate), polyamides and polysaccharides, and others of the above mentioned type of polymers being copolymers, linear/branched, and compounded compositions of the above with or without additives e.g. for adhesion, surface modification or fire retardation. In the present invention, the polymer is used in the form of a suitable precursor profile such as a tape or ribbon. The terms tape or ribbon are used herein to describe a unitary filament preferably in the form of a narrow strip of material with continuous coherent structure unlike the multifilament fibers obtained by e.g. solution spinning. For some applications, the precursor profile can be a monofilament, sheet or tube. For all embodiments, the precursor material is placed in a non-volatile solvent at high temperatures, near the polymer crystalline melting point for 1–5 minutes to form a pseudo-gel. Then cooling the pseudo-gel e.g. tape profile under controlled conditions to ambient temperature, lightly compressing the tape between rolls to remove the non-volatile solvent by squeezing action, removing the residual solvent from the tape by extraction with a volatile solvent and then by evaporation or vacuum, and then compressing the profile between rolls to remove defects on the tape, balance its porosity, increase its crystallinity, by up to 10%, improve its coherence and continuity, and then increase its tensile properties by predrawing to a draw ratio of 3–6 and eliminate necking. The processed tape precursor is then stretched to a certain draw ratio at temperatures below the crystalline melting point of the polymer in order to obtain certain desired mechanical properties. Resulting products could then be used in single filament form or be braided, knitted, or woven, and also incorporated into composite products.

The final fiber products of our process can be used as dental floss, fishing line, sail cloth, ropes, threads, bondable tapes, porous membranes, structural and reinforcing material, in catheters and balloon materials, etc. They can also be used in composite materials with glass, carbon, mica, aromatic polyamide fibers, steel, silicon, boron nitride, and other inorganic and ceramic fibers for impact resistance and as bullet-proof or ballistic resistant materials.

Other objects, advantages and features of the invention will become apparent from the following detailed description including examples of product development according to the invention.

DETAILED DESCRIPTION OF EMBODIMENTS

In accordance with the present invention the precursor material is a thermoplastic polymer meeting certain requirements i.e. the polymer must be linear with molecular weight greater than 300,000 to 6 million and be capable of being: a) solid state deformed into high modulus and strength fibrous products, and b) swollen with a solvent and forming a pseudo-gel state. Polymers suitable for precursor material include polyethylenes, polypropylenes, polyamides, polyesters, polymethyl pentene, polyvinyl alcohol, poly acrylonitrile, polysaccharides, and variation of such polymers, including copolymers, linear/branched, compounded compositions with or without additives. In one form, the precursor material may be prepared by melt crystallization using compression molding and skiving or direct melt extrusion into tapes and ribbons. Here, a continuous solid piece of material is formed from either of these approaches.

The precursor material could also be prepared by powder compaction under selected temperature and pressure conditions. For polyethylene, suitable temperatures are in the range of 80° C. to 240° C. and pressures from 1000 psi to 60,000 psi. Our process can use either an ultra-high molecular weight polyethylene powder or mixtures of powders which can be fed through a converging conical die, or between extrusion rolling dies or rolls, to produce continuous and coherent structures. For example, UHMWPE HiFax 1900; Mw=3–4×10$^6$, reactor powder was compacted under a pressure of around 2,000 psi at 110° C. into 1 mm thick and 10 mm wide tapes. The so prepared tapes were then drawn to a draw ratio 6 by compression at 124° C. through a pair of rollers.

The precursor material originally provided as described can be processed directly into a tape, ribbon, sheet, rod, monofilament, tube, and any other geometrical profile by skiving or by ram or melt extrusion.

After forming the original precursor material, it may be drawn into an oriented ribbon/tape/sheet/rod/monofilament of a desired size and cross section as was described briefly above.

Now, the tape/ribbon/sheet of the previous step is fed into a solvent (volatile or non-volatile) unoriented or after orientation by stretching or compression drawing through rollers to form a swollen pseudo gel structure. The solvent could be paraffin oil, mineral or vegetable oils, decalin, xylene, and kerosene. Preferably the tape/sheet is swollen at 130°–160° C. in paraffin oil to provide a change in weight Ws/Wp (weight of solvent to weight of polymer) of about 3 to 5, and not exceeding 10 when swollen for longer times. For example, swelling of a precursor polyethylene tape with paraffin oil at 130° C. for 5 minutes, provided a change in weight of 170%, a change in length of 50%, a change in width of 15%, and change in thickness of 20%. Depending on the thickness, the solvent can go across the thickness of the tape/ribbon/sheet, or only at the surface. Thus, the process does not involve formation of a solution. Under the employed swelling conditions, the molecular chain mobility is restricted by molecular entanglements and crystals (the swollen polymer has a residual crystallinity of up to 18%), resulting in a semicrystalline state which has a reduced molecular entanglement density. The amount of swelling to make pseudo-gels can also be controlled by the starting crystallinity of the polymer profile. A lower crystallinity, resulting in a higher amorphous region, allows more swelling. It has been observed that when the precursor tape/ribbon/sheet is frozen using liquid nitrogen, and then exposed to a solvent, say at room temperature, it swells faster to form a pseudo-gel structure described above.

The swollen tape/ribbon/sheet in its pseudo-gel state is then cooled down below 70° C. by quenching or slow cooling to recrystallize on present crystals and crystal nuclei.

Subsequently, the swollen pseudo-gel material is lightly compressed to remove the non-volatile solvent by mechanical means such as rolling the tape/ribbon/sheet between soft rolls. For example, after swelling at 130° C. for 5 minutes, almost 90% of the paraffin oil will be removed by this light compression step.

Thereafter, the tape/ribbon/sheet of the previous step is fed in a volatile solvent, e.g. hexane. For example, after the swollen tape has been in paraffin oil at 130° C. for 5 minutes, and is then compressed, it is fed in a hexane bath at room temperature for up to 10 minutes to remove any residual paraffin oil. Higher temperatures can be used for faster removal of this oil, if desired.

In the next step, any residual volatile solvent is removed by evaporation or vacuum to provide a dried tape.

Now, the dried tape is compressed between rolls at suitable temperature (room temperature to 130° C.) and pressure (100 to 50,000 psi) conditions without or with stretching it to a deformation ratio of about 6 to produce a uniaxially oriented tape before its final hot stretching.

Compression-rolling the dried tape before final stretching gives the following desired characteristics: removal of defects in the tape, provides balance porosity and better homogenization and increases crystallinity (by about 1–10%) which is known to result in better mechanical properties. Also, pre-drawing the tape to a draw ratio up to 6 gives the precursor tape better strength and mechanical stability before its final drawing, and results in a fibrous tape product with better mechanical properties. Compression-rolling also makes a more coherent and continuous structure. In addition, predrawing makes the precursor tape more coherent and provides a continuous structure. It also eliminates necking thus enabling one to better draw and obtain higher final properties.

Thereafter, the compressed tape/ribbon/sheet may be stretched at 80°–130° C. at different draw rates from 0.5 to over 100 of feet/min using single or multiple stages in conventional drawing apparatus. The compression and drawing steps of the processed material accomplishes the orientation, unfolding and extension of the molecular chains and provides a unitary filament end product with exceptional strength and high modulus characteristics.

The single filament products resulting from the previous method steps may also be braided, knitted, or woven, as commercial materials, and also incorporated to form composite products.

The filament products provided by the aforesaid process steps can be used as dental floss, fishing line, sail cloth, ropes, threads, bondable tapes, porous membranes, structural and reinforcing materials, catheters and balloon materials, etc.

Braided, knitted or woven products made from combinations of single filaments can be used as composite materials in combination with glass, carbon, mica, (Kelvar®), steel, silicon, boron nitride, and other inorganic and ceramic fibers for impact resistance and as bullet-proof or ballistic resistant materials.

The following examples illustrate various implementations of the method according to the present invention including examples of products resulting from different application of the method.

EXAMPLE 1—DENTAL FLOSS

A new dental floss product with a unique combination of properties, was made of a very high molecular weight (MW) polyethylene, preferably with MW greater than 300,000 and even better with MW greater than 1,000,000. It was discovered that such polyethylenes, particularly those with molecular weights greater than 1 million have self-lubricating properties and can be drawn into highly oriented and extended tape products suitable as dental floss. Such products are fibrillar, but unlike the conventionally available products, are not multifilament and they exhibit remarkable resistance to shredding. The properties of such fibrillar products vary depending on the degree of chain extension as effected by the draw ratio, and on other processing conditions according to the method.

Healthy gums and bone anchor teeth firmly in place. Gingivitis occurs when toxins from bacteria-laden plaque irritate the gums, causing them to be red and tender and to bleed. Periodontitis is the more advanced stage. Toxins destroy more tissue, gums become detached from the teeth, roots and bone are exposed, leading to tooth loss. Plaque is constantly forming on tooth surfaces. If not removed daily, plaque can cause cavities and gum disease. Toothbrushing alone cannot remove plaque from all tooth surfaces. Flossing helps remove plaque between teeth and below the gums.

Dental floss products heretofore developed and available in the market have well known problems and disadvantages such as: shredding of the floss on use into separate filaments resulting in ineffective flossing and breakage; slippage of the fiber between teeth making it hard to use and making flossing ineffective. Most of the prior art floss products are made from nylon, polyamides, or teflon and suffer disadvantages in mechanical properties compared to newer materials.

In order to hold the fibers from shredding, many prior art floss products were coated with wax. More recently a polytetraflouroethylene type of material was produced with slipping characteristics. This material did not shred readily, but, it had a very low tensile strength in comparison to other floss materials.

As indicated, the present invention provides a new dental floss tape product with a unique combination of properties. The dental floss is made of a very high molecular weight (MW) polyethylene, preferably with MW greater than 300,000 or preferably with a MW greater than 1,000,000. Such polyethylenes, particularly those with molecular weights greater than 1 million have self-lubricating properties and can be drawn into highly oriented and extended tape products. Such products are fibrillar. However, they exhibit remarkable resistance to shredding. The properties of such products may vary somewhat depending on the degree of chain extension as effected by the draw ratio, and also on the processing conditions.

The new dental floss tape product of this example was made in accordance with the method steps of the present invention using a polyethylene capable of being swollen into a gel-like state in volatile or non-volatile solvents and having an average molecular weight of 0.8 to 3 million. In accordance with the invention, useable polyethylenes can be of a homopolymer nature, copolymer, or mixture of different molecular weight characteristics, e.g., a mixture of a resin of MW 800,000 and MW 3 million. Here, the dental floss product was prepared from a melt crystallized precursor tape of such a polyethylene which was first swollen into a gel-like state with paraffin oil at 130° C. for 1 minute, then was compressed (squeezed) lightly to remove the paraffin oil. It was then immersed in hexane for 5 minutes to dry the tape and remove all residual paraffin oil. Thereafter, the tape was heated to around 70° C. to remove all residual hexane to produce a porous tape product with higher porosity than the original melt crystallized tape. Next, the porous tape was compressed under 100–10,000 psi using die rollers to balance the material physical properties, e.g., percent crystallinity, and pores uniformity. After compression, the tape was stretched with conventional drawing apparatus at a temperature of 80°–130 C. to obtain a drawn product with desired mechanical properties for dental floss.

As stated, swelling the polyethylene prior to drawing makes it porous. This porosity can be controlled by the applied swelling Conditions and by the compression conditions between the die rollers before stretching the polyethylene. By making the polyethylene porous, one can incorporate different additives such as flavor enhancers or medicinal materials either while it is being swollen by placing the additive in the paraffin oil or subsequently after the solvent has been removed.

The product of this invention is a tape acting like a monofilament in sharp contrast to the multifilament dental floss products heretofore available. Thus, the product is easier and more convenient to use, has a higher resistance to tearing, does not fibrillate into smaller filaments, thereby making flossing more convenient and effective.

In summary, a product formed from high molecular weight polyethylene material according to the invention, provides several advantages:

1. Since our floss product is in the form of a ribbon/tape, as opposed to a fiber, it makes flossing much easier. The product will not shred into filaments on prolonged use between teeth.
2. An extended range of Young's modulus and tensile strengths are available, e.g. the floss can be made precisely with Young's modulus in the range of 0.5 GPa to 10 GPa, and tensile strengths of 0.1 GPa to 1.2 GPa, thereby allowing a wide window for specific floss properties.
3. The floss can be made in any desirable range of widths, e.g. from 0.01 inches to 0.25 inches and more.
4. The floss can be made in any desirable range of thickness, e.g. from 0.001 inches to 0.005 inches and more.
5. The floss can be made in a range of flavors such as neutral, mint, chocolate, strawberry, almond, orange, lemon, banana, maple, etc.
6. The floss can be treated or permeated with medicinal materials such as peroxide which disinfects the material and makes it safer for use in the mouth, and/or attack the residual bacteria between the gums and thus prevent plaque formation.
7. The resulting porosity of the dental floss tape can be used to incorporate additives, flavors, anti-bacterial agents, anti-tartar agents, and drugs for periodontal diseases.
8. Another advantageous property of the dental tape or floss made in accordance with the invention is that it is not coated with a waxy solid but is self lubricating and is highly effective in use.

EXAMPLE 2—FISHING LINE

A new fishing line with a unique combination of properties, was made of a very high molecular weight (MW) polyethylene having a MW of about 1.45 million. The starting profile was a rod of diameter 0.020" and was swollen in paraffin oil for 2 minutes at 130° C., then lightly compressed to remove the paraffin oil, then dried in hexane to remove any remaining paraffin oil, and finally drawn at 130° C. to a desired diameter by drawing to different extents.

The fishing lines used currently are made of nylon or dacron. For the same diameter of line, the fishing line made in accordance with the present invention is stronger and has lower elongation at failure.

In particular the fishing line made in accordance with the present invention provides several important advantages and features. It provides a line with a small diameter yet high strength, light weight, and having a low stretch factor. The line can be easily knotted, will float, and casts well. It does not absorb water or swell on the reel, is self-lubricating, and does not fray. Following are comparative strength versus size comparisons with samples made from nylon.

| Strength versus Size | | |
|---|---|---|
| Diameter | Nylon | Present Invention |
| 0.009 inch | 8 lbs | 25 lbs |
| 0.012 inch | 10 lbs | 40 lbs |
| 0.017 inch | 15 lbs | 70 lbs |
| Elongation | | |

Nylon 25-35% elongation at failure
Present Invention 5-10% elongation at failure

EXAMPLE 2a—FISHING LINE

A highly oriented tape of a very high molecular weight polyethylene (Mw~1.45 million) was obtained by the process described in Example 1. However, the stretching step involved drawing the tape to different extents. The drawn tape was twinned and braided into a line incorporating four filaments. For the purpose of this example, the tape was twinned first by twisting slowly the tape on a lathe and then by braiding the twisted tapes into a four component structure.

EXAMPLE 3—HIGH MOLECULAR WEIGHT POLYETHYLENE

A precursor powder material having a MW of 1.45 million was used. This powder was compressed at 200° C. and 10.000 psi to make a cylindrical billet. Tapes of width 0.25 inches and thickness 0.010 inch were skived from this block. The tape was swollen in paraffin oil for 1 minute at 30° C., lightly compressed to remove paraffin oil, dried in hexane to remove remaining paraffin oil. The dried tape was compressed under 20,000 psi, and then stretched at 30° C. The stretched tape had a draw ratio of 42, and the final material properties included a Young's modulus of at least 55 GPa and tensile strength of at least 1.2 GPa.

EXAMPLE 4—POWDER COMPACTED POLYETHYLENE

Precursor material in the form of a UHMWPE Hoechst Celanese GUR 412 powder was compacted into a tape under 3,000 psi at 120° C. The tape was swollen in paraffin oil at 130° C. for 2 minutes. The change in weight was 190% increase in length 13%, in width 8%, and thickness 30% on swelling. The tape was then lightly compressed to remove paraffin oil, the remaining paraffin oil was extracted by hexane, and the tape was stretched at 130° C. to a draw ratio of 18, resulting in final properties of Young's modulus of 12 GPa, tensile strength of 0.5 GPa, and percent elongation at break of 5%.

EXAMPLE 5—POWDER COMPACTED POLYETHYLENE (SOLID-STATE ROLLING FOLLOWED BY HOT STRETCHING)

Precursor material in the form of a UHMWPE HiFax (Himont 1900; Mw~3-4 million) reactor powder was compression molded at 2,000 psi at 110° C. into 1 mm thick and 10 mm wide tapes. The so prepared tapes were compression deformed at 124° C. to a draw ratio 6 by rolling through a pair of rollers rotating at a speed e.g. 30cm/min. The so prepared pre-drawn tapes by rolling, were then stretched uniaxially at 130° C. to a final fibrous tape product with a Young's modulus of at least 68 GPa and tensile strength of at least 1.3 GPa. The Table below lists the properties of the precursor compacted powder before and at different stages of draw by compression rolling and stretching.

TABLE

Physical and Mechanical Properties of Himont 1900 UHMWPE precursor compacted powder before and during different stages of draw by compression rolling and stretching.

| Item/step | Draw | Crystal-linity % | Melting Temp. (°C.) | Y.M.# (GPa) | T.S.## (GPa) |
|---|---|---|---|---|---|
| 1. Compacted powder | 1 | 73.4 | 142.4 | * | * |
| 2. Hot rolled | 6 | 67.9 | 141.8 | 2.8 | 0.38 |
| 3. After hot | 73 | 81.7 | 145.1 | 68 | 1.3 |

*Too fragile to measure
Young's modulus
Tensile strength

EXAMPLE 6—POLYPROPYLENE TAPE

An ultra-high molecular weight polypropylene tape was skived from a block made by melt crystallization during compression molding. The untreated tape had a melting temperature of 163° C. This 0.005 inch thick tape was swollen in paraffin oil at 160° C. for 2 minutes to form a pseudo-gel and the paraffin oil was then extracted by hexane. During swelling, the change in weight of the tape was 166%, increase in length 12%, increase in width 8%, and thickness 33%. The dried tape was stretched at 130° C. to a draw ratio of 7, resulting in final tape properties of Young's modulus of at least 3 GPa and tensile strength of at least 0.3 GPa.

EXAMPLE 7—HIGH DENSITY POLYETHYLENE

A precursor material with a 800,000 molecular weight polyethylene powder, was compressed at 200° C. and 10,000 psi to make a cylindrical billet. Tapes of width 0.25 inches and thickness 0.010 inch were skived from this block. The tape was swollen in paraffin oil for 1 minute at 125° C., lightly compressed to remove paraffin oil, dried in hexane to remove remaining paraffin oil, compressed under 20,000 psi to even the material, and stretched at 125° C. The stretched tape had a draw ratio of 38, and the final material properties included a Young's modulus of at least 32 GPa and tensile strength of at least 0.8 GPa.

EXAMPLE 7(a)—HIGH DENSITY POLYETHYLENE

The same procedure as in Example 7 was used with a precursor material of 500,000 molecular weight polyethylene and was produced directly into a tape of width 1 inch and thickness 0.010 inches by melt extrusion. The product, obtained on stretching to a draw ratio of 9 had a Young's modulus of at least 3 GPa and a tensile strength of at least 0.5 GPa.

Using the steps of Examples 3, 4, 5 and 7 products in the form of tapes may also be woven into fabrics which have characteristics of light weight, relatively high porosity, high strength, water and cold temperature resistance, and good wear and tear resistance.

To those skilled in the art to which this invention relates, many changes in construction and widely differing embodiments and applications of the invention will make themselves known without departing from the spirit and scope of the invention. The disclosure and the description herein are purely illustrative and are not intended to be in any sense limiting.

What is claimed is:

1. A dental floss comprised of a unitary filament of high molecular weight polyethylene material having a molecular weight of at least 300,000, a Young's modulus in the range of 0.5 GPa to 10 GPa and a tensile strength of 0.1 GPa to 1.2 GPa.

2. The dental floss as described in claim 1 having a molecular weight in the range of 0.3 to 6 million.

3. The dental floss as described in claim 1 in the form of a tape having a width in the range of 0.01 to 0.25 inches and a thickness in the range of 0.001 to 0.005 inches.

4. The dental floss as described in claim 1 wherein said unitary filament is permeated with a flavor enhancing agent.

5. The dental floss as described in claim 1 wherein said unitary filament is permeated with a preselected medicinal agent.

* * * * *